(12) United States Patent
Tsubouchi

(10) Patent No.: US 10,918,367 B2
(45) Date of Patent: Feb. 16, 2021

(54) HEART ROTATOR

(71) Applicant: TERUMO CARDIOVASCULAR SYSTEMS CORPORATION, Ann Arbor, MI (US)

(72) Inventor: Takeshi Tsubouchi, Dexter, MI (US)

(73) Assignee: Terumo Cardiovascular Systems Corporation, Ann Arbor, MI (US)

(*) Notice: Subject to any disclaimer, the term of this patent is extended or adjusted under 35 U.S.C. 154(b) by 95 days.

(21) Appl. No.: 16/266,182

(22) Filed: Feb. 4, 2019

(65) Prior Publication Data

US 2019/0167247 A1 Jun. 6, 2019

Related U.S. Application Data

(63) Continuation of application No. PCT/US2017/048313, filed on Aug. 24, 2017.

(60) Provisional application No. 62/378,741, filed on Aug. 24, 2016.

(51) Int. Cl.
*A61B 17/02* (2006.01)
*A61B 17/00* (2006.01)
*A61B 17/30* (2006.01)

(52) U.S. Cl.
CPC ...... *A61B 17/0218* (2013.01); *A61B 17/0206* (2013.01); *A61B 2017/00314* (2013.01); *A61B 2017/00561* (2013.01); *A61B 2017/00946* (2013.01); *A61B 2017/0237* (2013.01); *A61B 2017/308* (2013.01)

(58) Field of Classification Search
CPC ............ A61B 17/0218; A61B 17/0206; A61B 2017/0237; A61B 2017/00314; A61B 2017/308; A61B 2017/00946; A61B 2017/00561
USPC .......................................................... 600/37
See application file for complete search history.

(56) References Cited

U.S. PATENT DOCUMENTS

| | | | |
|---|---|---|---|
| 5,709,679 A * | 1/1998 | Essig | A61B 18/1482 128/898 |
| 6,764,444 B2 | 7/2004 | Wu et al. | |
| 6,973,347 B1 * | 12/2005 | Ben-Haim | A61B 5/0422 600/16 |
| 2001/0041827 A1 * | 11/2001 | Spence | A61B 17/0218 600/201 |
| 2002/0045799 A1 * | 4/2002 | Lau | A61M 1/1003 600/37 |

(Continued)

*Primary Examiner* — Navin Natnithithadha
*Assistant Examiner* — Sunita Reddy
(74) *Attorney, Agent, or Firm* — Darryl Newell; MacMillan, Sobanski & Todd, LLC

(57) ABSTRACT

A heart rotator tool uses a malleable guide rail with a distal end adapted to conform to a desired shape along a surface of a heart tissue. A suction cup is adapted for grasping the heart tissue. A slider is slidably mounted on the guide rail which is flexible to conform to the shape of the guide rail while sliding, the slider having a distal end connected to the suction cup and having a proximal end for providing a handgrip. A vacuum tube is joined to the suction cup and carried by the slider. The vacuum tube is adapted to selectively (i.e., selectably couple a vacuum source to the suction cup. After arranging the guide rail around the heart and sliding the suction cup to a desired position, the vacuum is activated and subsequent sliding of the suction cup via movement of the handgrip rotates the heart as desired.

9 Claims, 4 Drawing Sheets

(56) References Cited

U.S. PATENT DOCUMENTS

| | | | |
|---|---|---|---|
| 2002/0052538 A1* | 5/2002 | Lau | A61M 1/122 600/37 |
| 2002/0058856 A1* | 5/2002 | Peng | A61B 17/02 600/37 |
| 2002/0082469 A1* | 6/2002 | Taheri | A61B 17/00234 600/37 |
| 2003/0139646 A1* | 7/2003 | Sharrow | A61B 17/02 600/37 |
| 2004/0002628 A1* | 1/2004 | Wu | A61B 17/0206 600/206 |
| 2004/0002630 A1* | 1/2004 | Wu | A61B 17/0206 600/210 |
| 2004/0002631 A1* | 1/2004 | Wu | A61B 17/0206 600/210 |
| 2004/0092985 A1* | 5/2004 | Parihar | A61B 17/3415 606/167 |
| 2004/0193004 A1* | 9/2004 | Tsubouchi | A61M 1/122 600/16 |
| 2005/0010197 A1* | 1/2005 | Lau | A61M 1/0066 606/1 |
| 2005/0054892 A1* | 3/2005 | Lau | A61F 2/2481 600/37 |
| 2005/0159650 A1* | 7/2005 | Raymond | A61B 17/3421 600/201 |
| 2005/0203334 A1* | 9/2005 | Lonky | A61B 17/00234 600/37 |
| 2006/0129026 A1* | 6/2006 | Wallin | B29C 70/766 600/37 |
| 2007/0015958 A1* | 1/2007 | Lau | A61B 17/00234 600/37 |
| 2007/0213734 A1* | 9/2007 | Bleich | A61B 17/1757 606/79 |
| 2007/0232864 A1* | 10/2007 | Sharp | A61B 17/0293 600/227 |
| 2008/0015408 A1* | 1/2008 | Paolitto | A61B 17/11 600/37 |
| 2008/0139879 A1* | 6/2008 | Olson | A61B 17/02 600/37 |
| 2008/0181733 A1* | 7/2008 | Wright | B23Q 9/0042 408/1 R |
| 2008/0269550 A1* | 10/2008 | Wright | A61B 17/02 600/37 |
| 2008/0281150 A1* | 11/2008 | Wright | A61B 17/02 600/37 |
| 2009/0005794 A1* | 1/2009 | Lowry | A61B 17/0206 606/148 |
| 2009/0030270 A1* | 1/2009 | Arai | A61B 17/02 600/37 |
| 2009/0043152 A1* | 2/2009 | Lau | A61N 1/0587 600/37 |
| 2009/0048480 A1* | 2/2009 | Klenk | A61B 17/00234 600/37 |
| 2009/0281556 A1* | 11/2009 | Newell | A61F 5/0003 606/144 |
| 2009/0287227 A1* | 11/2009 | Newell | A61B 17/0401 606/148 |
| 2009/0299131 A1* | 12/2009 | Green, II | A61B 17/0206 600/37 |
| 2011/0098806 A1* | 4/2011 | Otto | A61M 1/1068 623/3.1 |
| 2011/0251450 A1* | 10/2011 | Pagani | A61M 1/3659 600/16 |
| 2012/0029271 A1* | 2/2012 | Meyer | A61B 17/0206 600/37 |
| 2012/0059457 A1* | 3/2012 | Leinsing | A61F 2/2466 623/2.11 |
| 2012/0253112 A1* | 10/2012 | Hjelle | A61F 2/2481 600/37 |
| 2012/0265082 A1* | 10/2012 | Hjelle | A61B 5/107 600/508 |
| 2012/0323262 A1* | 12/2012 | Ibrahim | A61B 17/12013 606/144 |
| 2013/0109924 A1* | 5/2013 | Gan | A61B 17/02 600/205 |
| 2013/0184520 A1* | 7/2013 | Lee | A61B 17/02 600/37 |
| 2013/0197559 A1* | 8/2013 | Hariton | A61B 17/3468 606/185 |
| 2013/0237768 A1* | 9/2013 | Heftman | A61B 17/0218 600/228 |
| 2013/0317925 A1 | 11/2013 | Zhao | |
| 2014/0081307 A1* | 3/2014 | Zavatsky | A61B 17/0218 606/190 |
| 2014/0107406 A1* | 4/2014 | Hjelle | A61F 2/2481 600/37 |
| 2014/0148641 A1* | 5/2014 | Greee, II | A61B 17/30 600/37 |
| 2014/0171733 A1* | 6/2014 | Sternik | A61B 17/12122 600/37 |
| 2014/0350554 A1* | 11/2014 | Keller | A61F 9/00754 606/45 |
| 2015/0216727 A1* | 8/2015 | Keller | A61B 18/082 606/29 |
| 2015/0366574 A1* | 12/2015 | Kovarik | B25J 1/02 600/104 |
| 2016/0302811 A1* | 10/2016 | Rodriguez-Navarro | A61B 17/10 |

\* cited by examiner

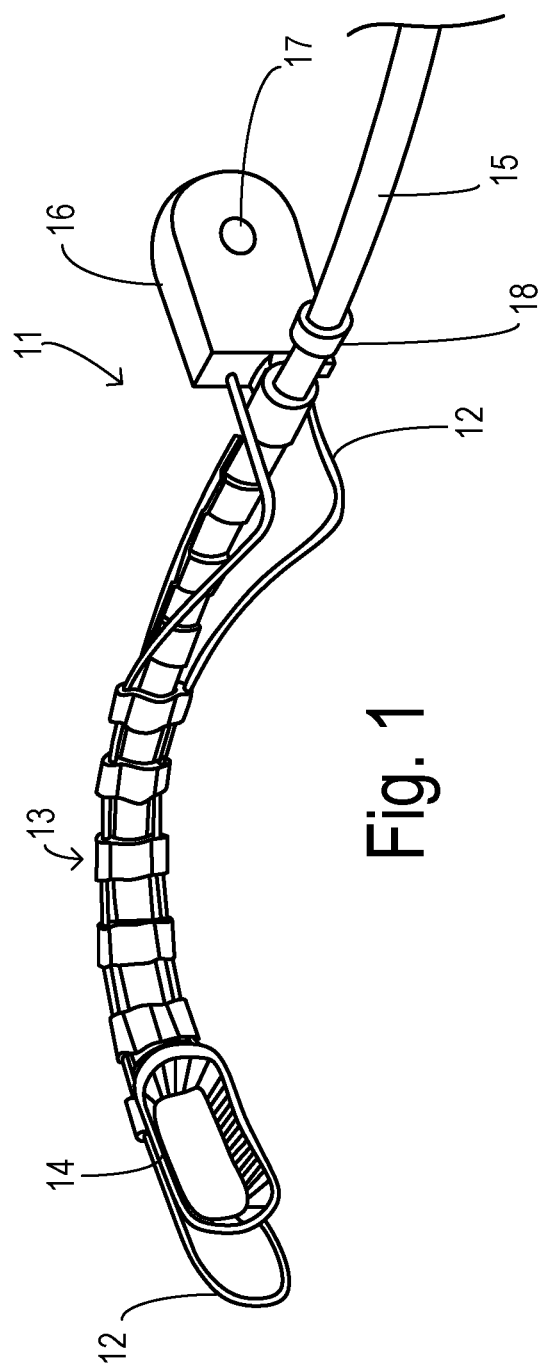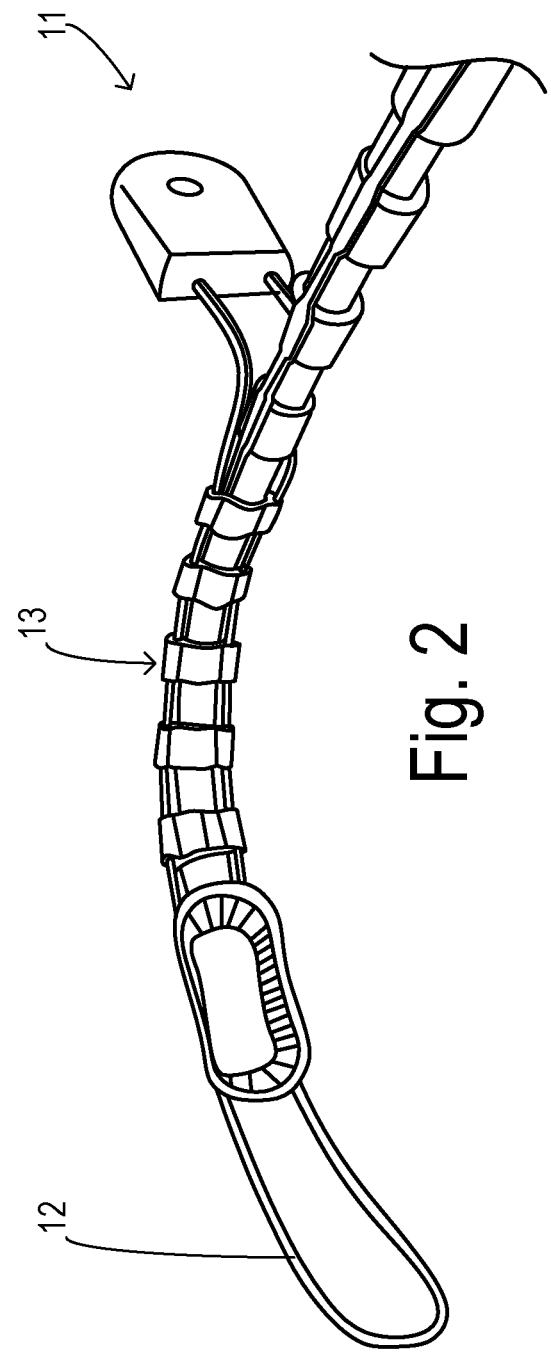

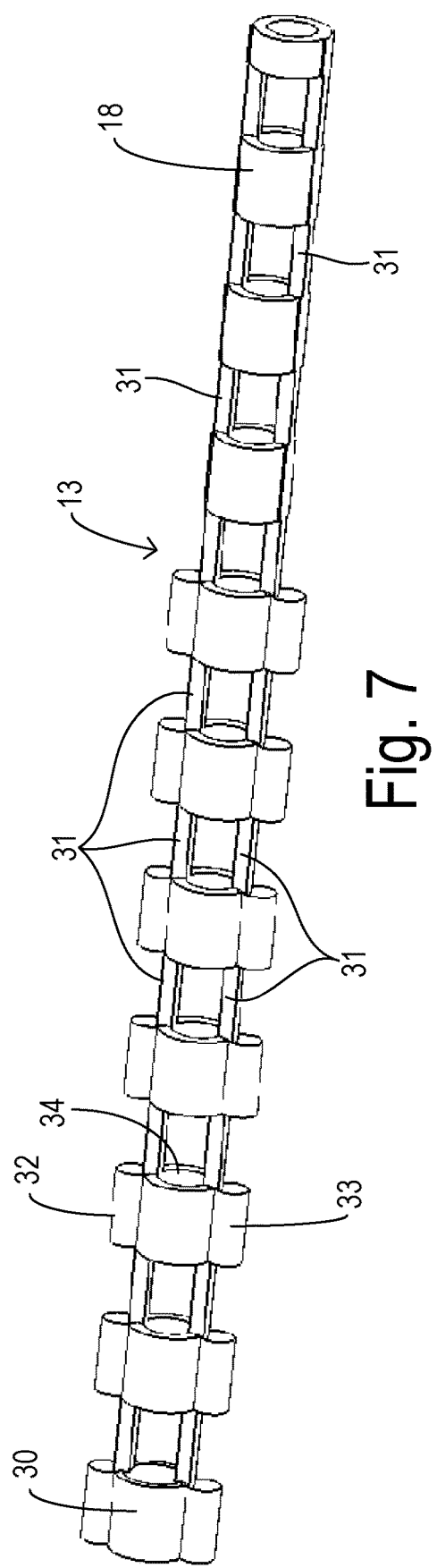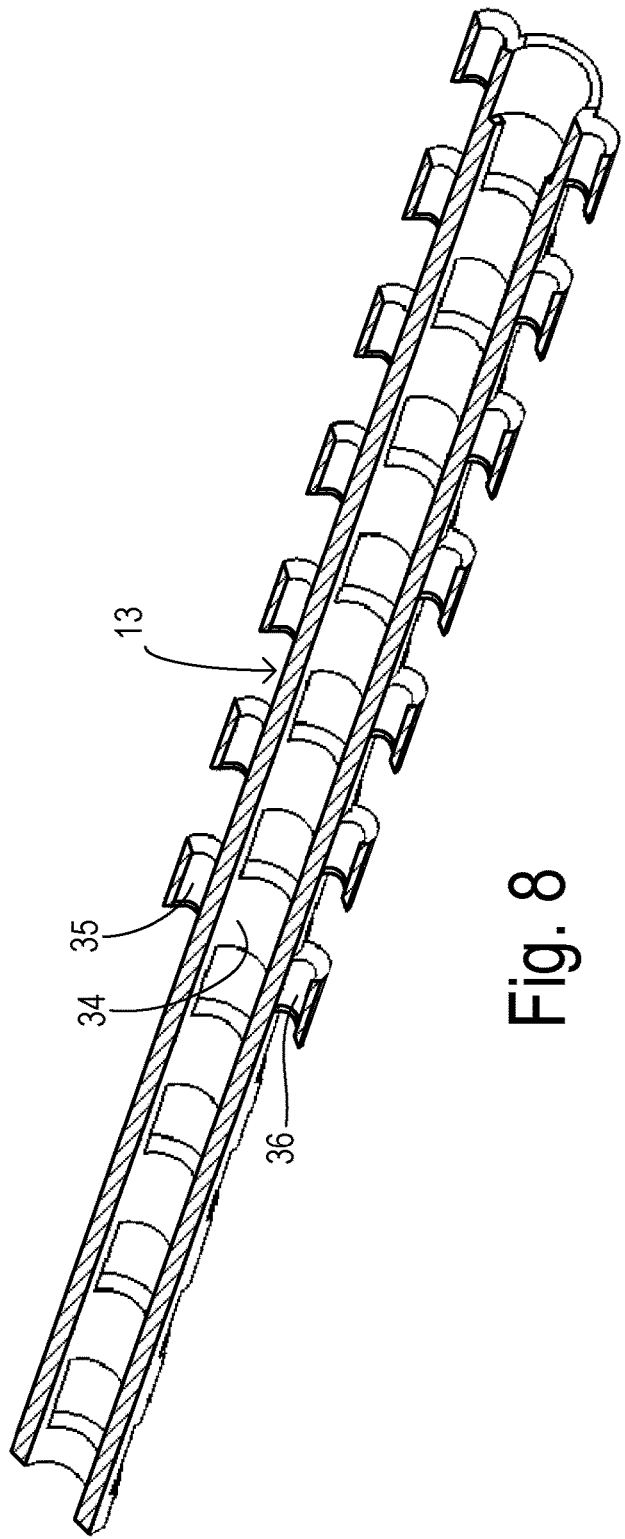

HEART ROTATOR

CROSS REFERENCE TO RELATED APPLICATIONS

This application is a continuation of PCT Application No. PCT/US2017/048313, filed Aug. 24, 2017, based on and claiming priority to U.S. provisional application Ser. No. 62/378,741, filed on Aug. 24, 2016, both of which are incorporated herein by reference in their entirety.

STATEMENT REGARDING FEDERALLY SPONSORED RESEARCH

Not Applicable.

BACKGROUND OF THE INVENTION

This invention is relates to a surgical tool for heart surgery, wherein the tool can be used in a vascular graft operation or coronary bypass while maintaining full tissue visibility and a working space for performing anastomosis. By attaching the tool to an arm of a sternal retractor, a surgeon can move (i.e., rotate) the heart in order to perform a bypass connection or secure an arch graft at a specific desired position achieving good visibility and enabling the suturing to proceed without additional human assistance.

In order to minimize incision and gain faster recovery, minimally invasive cardiothoracic surgery (MICS) is often performed. There are a few challenges to be addressed for performing MICS surgery, as compared to sternum open heart surgery. MICS is conducted using a very limited size opening and small overall space. In order to perform surgery through a small window, an ability to align a target operation area of the heart to match the window opening is a key for success. For example, it may often be essential to rotate the heart within the pericardium space in order to align a desired surgical area within the window. Since the size of the surgical opening is limited, however, the heart cannot be easily lifted and manipulated in order to gain access to a target area of the heart. A conventional technique to rotate the heart has used a suction cup mounted to the end of a solid bar, wherein vacuum is applied within the suction cup to grasp and manipulate the heart tissue from above. Multiple steps of grasping, moving, releasing, and grasping at another location has made this a difficult and time-consuming technique. Furthermore, an additional surgical entry hole into the patient may be required. Also, as a result of the solid shaft and the fixed shaft hole location, there are limitations in the available movements. Since the available movement is mainly a small straight pushing or pulling movement along the axis of the hole, it is very difficult to provide rotational motion to the heart. It would be desirable to eliminate any additional hole while providing easy manipulation through a main opening.

SUMMARY OF THE INVENTION

In one aspect of the invention, a heart rotator tool comprises a malleable guide rail with a distal end adapted to conform to a desired shape along a surface of a heart tissue. The invention includes a suction cup adapted for grasping the heart tissue. A slider is slidably mounted on the guide rail which is flexible to conform to the shape of the guide rail while sliding, the slider having a distal end connected to the suction cup and having a proximal end for providing a handgrip. A vacuum tube is joined to the suction cup and carried by the slider. The vacuum tube is adapted to selectively (i.e., selectably couple a vacuum source to the suction cup. After arranging the guide rail around the heart and sliding the suction cup to a desired position, the vacuum is activated and subsequent sliding of the suction cup via movement of the handgrip rotates the heart as desired.

BRIEF DESCRIPTION OF THE DRAWINGS

FIG. 1 shows one embodiment of a heart rotator tool of the invention with a suction cup extended to a position close to the distal end of a guide rail.

FIG. 2 shows the heart rotator tool of FIG. 1 with the suction cup having been moved to a position intermediate of the distal and proximal ends of the guide rail.

FIG. 7 is a plan view of the slider of the rotator tool of FIG. 1.

FIG. 8 is a horizontal cross-sectional view of the slider of FIG. 7.

DETAILED DESCRIPTION OF PREFERRED EMBODIMENTS

Figure 3:
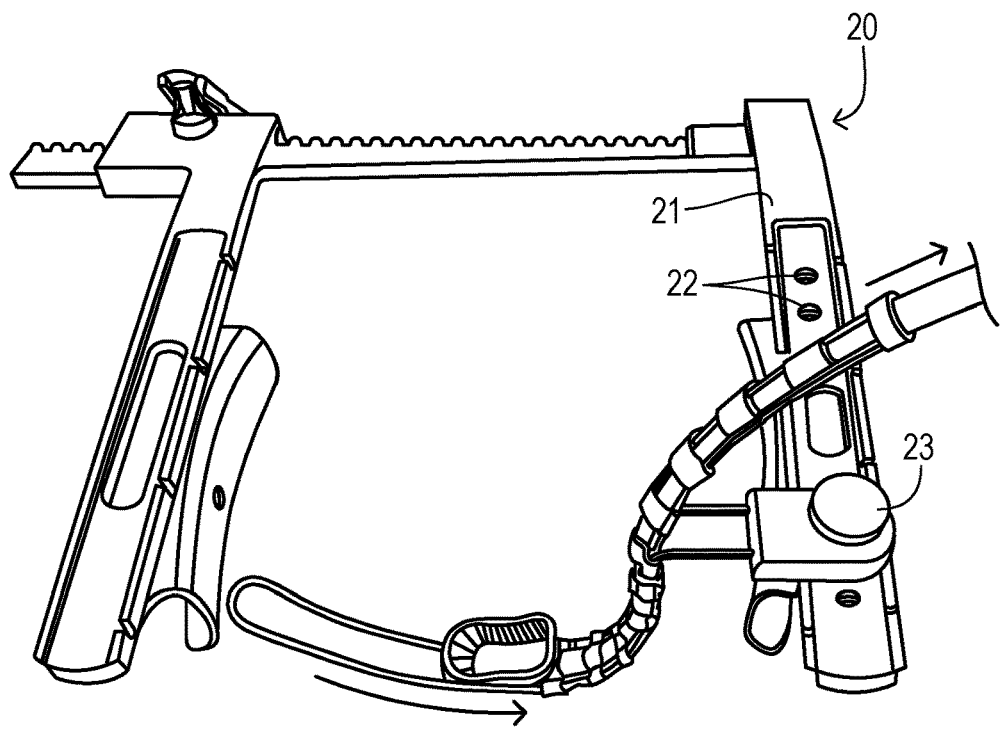
FIG. 3 is a perspective view of the heart rotator tool mounted to a sternal retractor frame.

Tools for manipulating the heart during MICS need to have enough adjustability and flexibility in order to accommodate many variations in body size, fat tissue thickness, and target area variations. This invention provides a rotator tool with a vacuum suction cup, tubing for delivering vacuum, a malleable rail, and a slider that rides along the rail and carries the cup. The slider may include a channel for the vacuum tube and one end of the slider provides a handle to manipulate the cup. The flexible/malleable rail can accommodate the tool according to the many variations of anatomy and the surgical needs.

FIGS. 1 and 2 are perspective views showing a heart rotator tool 11. A guide rail 12 is preferably formed as an elongated loop which may be comprised of a flexible plastic which can fit along with necessary shape, or more preferably is comprised of a malleable metal (including, for example, stainless steel, titanium, nickel-titanium, and others) which can be manually bent according to a desired shape (e.g., arc). Thus, rail 12 can be shaped to provide a penetration profile that wraps around a portion (e.g., an underside) of the heart while entering along the side of a single opening for minimally invasive surgery. The looped shape of rail 12 results in two generally parallel side runners which are received in concentric openings (e.g., side channels) of a slider 13. A suction cup 14 is firmly mounted at a distal end of slider 13 and has a fitting for receiving a vacuum tube 15. Slider 13 has an inner vacuum tube channel for carrying vacuum tube 15. When a vacuum pressure is applied to a proximal end of tube 15, it generates a vacuum within suction cup 14 for grasping the heart tissue.

At its proximal end, rail loop 12 is retained by a base 16 having a mounting hole 17 adapted for attaching to the sternal retractor frame after rail 12 has been appropriately bent into the desired shape and the distal end of rail 12 has been appropriately inserted beneath the heart tissue. A proximal end 18 of slider 13 forms a handgrip or handle to allow manipulation of slider 13 such that it moves along rail 12 between an extended position shown in FIG. 1 and a retracted position shown in FIG. 2.

Figure 4:
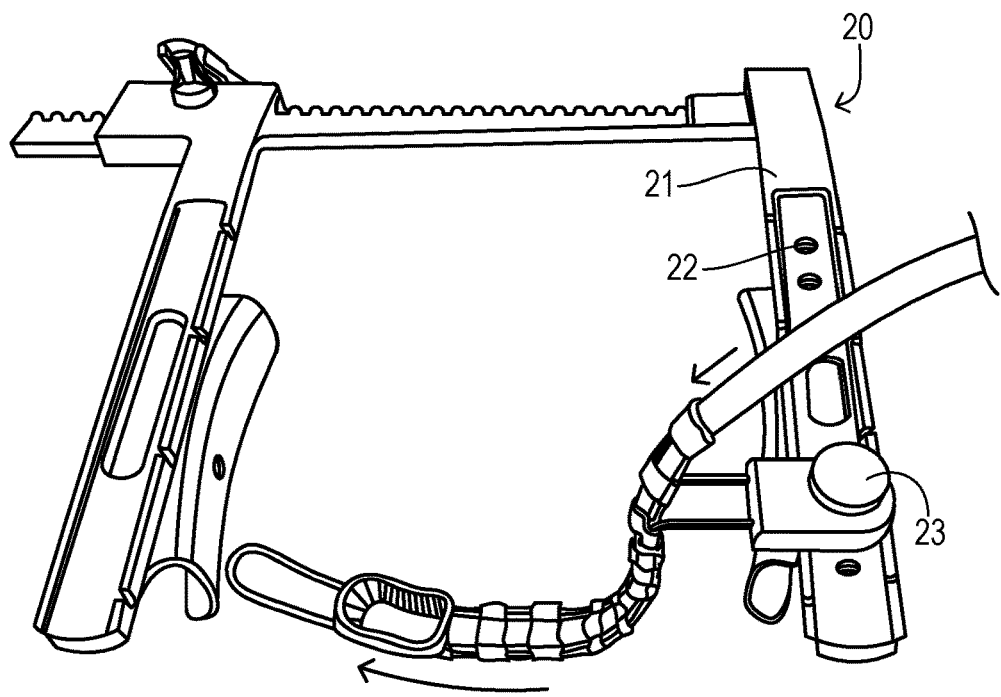
FIG. 4 is a perspective view of the rotator tool of FIG. 3 with the suction cup slid to another position.

FIGS. 3 and 4 show rotator tool 11 mounted to a sternal retractor frame 20 and being moved between extended (FIG. 4) and retracted (FIG. 3) positions. Suction generated at the suction cup grasps the heart so that sliding of the slider along the rail (i.e., pushing and pulling on the handle) causes the heart to rotate in the illustrated directions.

Retractor frame 20 includes a side plate 21 having a series of threaded holes 22 which are used to mount various surgical support components or tools such as a stabilizer arm. For the rotator tool of the invention, a threaded thumb screw 23 rigidly mounts the tool to plate 21 by passing it through mounting hole 17 and advancing it into one of the plate holes 22.

Figure 5:
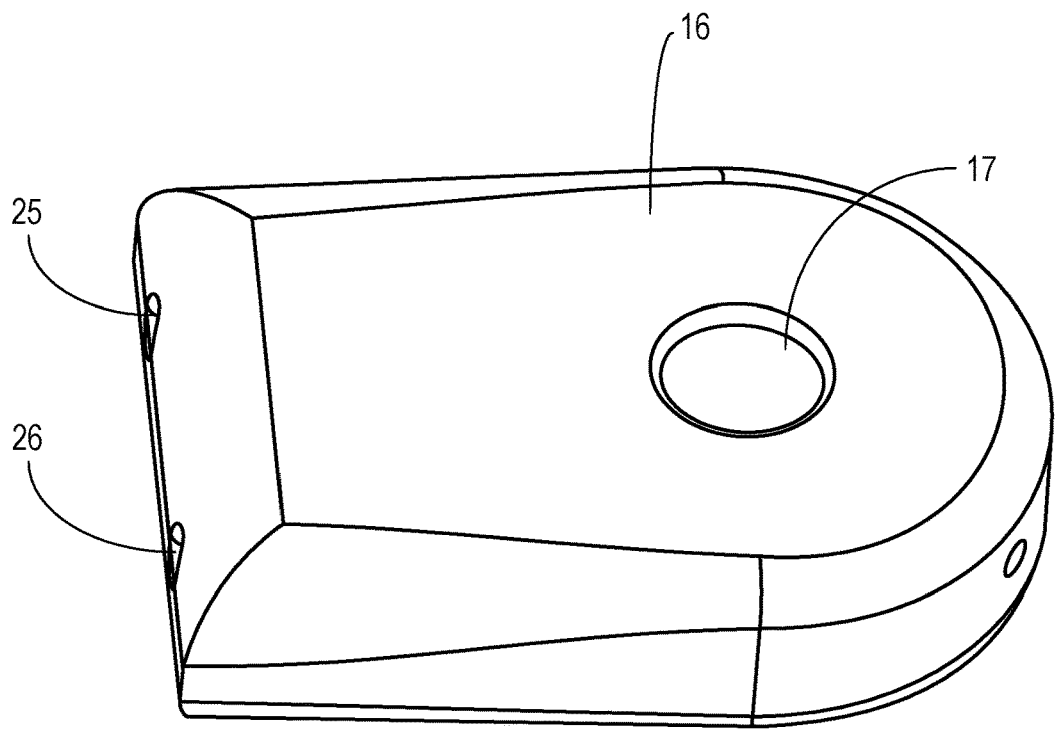
FIG. 5 is a perspective view of the base of the rotator tool of FIG. 1.
Figure 6:
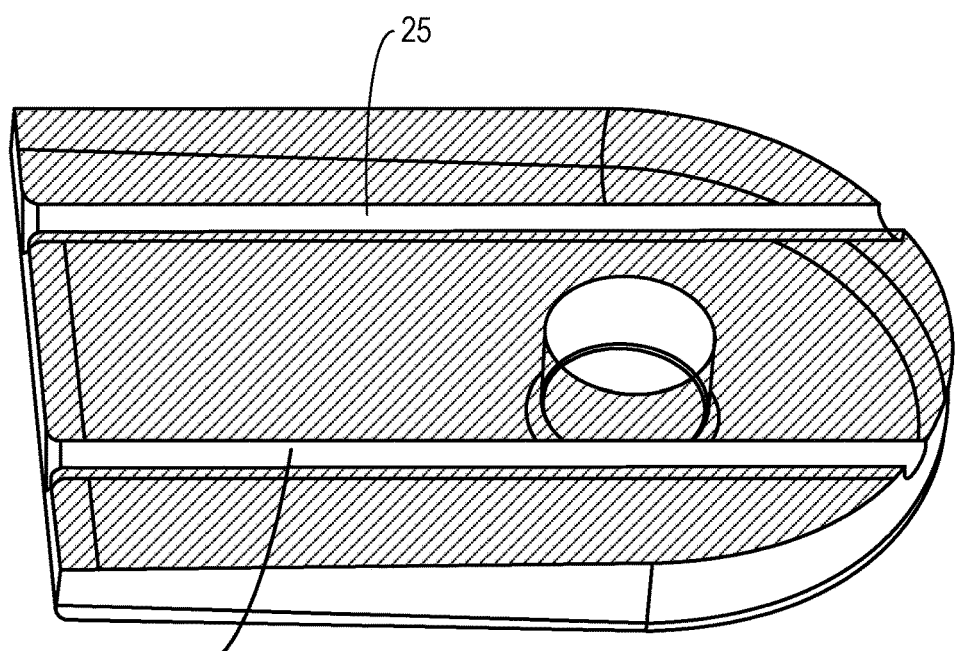
FIG. 6 is a horizontal cross-sectional view of the base of FIG. 5.

FIGS. 5 and 6 show base 16 in greater detail. A pair of internal bores 25 and 26 receive the proximal ends of the malleable rail. Base 16 may be comprised of molded thermoplastic. Bores 25 and 26 may be sized to provide an interference fit for the ends of the wire forming the guide rail.

FIGS. 7 and 8 show slider 13 in greater detail, comprising a handle end 18 and a distal end 30 with multiple channel segments serially joined by respective intervening links 31. Each segment in a first group of the channel segments adjacent the suction cup (i.e., located at distal end 30) includes side wings 32 and 33 with aligned guide rail channels 35 and 36 for slidably receiving the guide rail side runners and internal channels 34 for carrying vacuum tube 15. A second group of segments and links at the proximal end of slider 13 forming the handgrip do not include guide rail channels but do include vacuum tube channels 34. Slider 13 is preferably comprised of a flexible material (e.g., soft rubber) allowing it to follow the shape determined by the malleable rail. An extreme distal end segment 30 may be affixed to the suction cup by gluing or other mechanical means.

The guide rail and/or slider may be flexible or malleable over their entire length. Alternately, they can be comprised of alternating hard and flexible/malleable segments. The flexible segments can also be comprised of hinges between hard or soft segments.

What is claimed is:

1. A heart rotator tool comprising:
a malleable guide rail with a distal end, wherein the distal end is configured to conform to a desired shape along a surface of a heart tissue;
a suction cup adapted for grasping the heart tissue;
a slider slidably mounted on the guide rail which flexibly conforms to a shape of the guide rail while sliding, the slider having a distal end connected to the suction cup and having a proximal end for providing a handgrip; and
a vacuum tube joined to the suction cup and carried by the slider, wherein the vacuum tube is configured to selectively couple a vacuum source to the suction cup.

2. The rotator tool of claim 1, wherein the guide rail is comprised of a loop including generally parallel side runners.

3. The rotator tool of claim 2, wherein the loop is comprised of a malleable wire.

4. The rotator tool of claim 1 further comprising:
a base receiving a proximal end of the guide rail, wherein the base is configured to be rigidly mounted to a sternal retractor frame for minimally invasive cardiothoracic surgery on a patient.

5. The rotator tool of claim 1, wherein the slider is comprised of a plurality of channel segments serially joined by a plurality of intervening links, wherein the channel segments have a respective vacuum tube channel.

6. The rotator tool of claim 5, wherein a first group of the channel segments adjacent the suction cup each have at least one respective guide rail channel receiving the guide rail.

7. The rotator tool of claim 6, wherein a second group of the channel segments corresponding to the handgrip are unconnected from the guide rail.

8. The rotator tool of claim 5, wherein the slider is comprised of molded rubber.

9. A method of rotating a heart during minimally invasive cardiothoracic surgery, comprising the steps of:
arranging a bendable guide rail around the heart, the bendable guide rail being part of a rotator tool, wherein the bendable guide rail has a distal end, wherein the distal end is configured to conform to a desired shape along a surface of a heart tissue, wherein the rotator tool includes a suction cup adapted for grasping the heart tissue, and wherein the rotator tool includes a slider slidably mounted on the bendable guide rail which flexibly conforms to a shape of the bendable guide rail while sliding, the slider having a distal end connected to the suction cup and having a proximal end for providing a handgrip;
sliding the suction cup to a position in contact with the heart;
applying a vacuum to the suction cup so that it is releasably attached to the heart, wherein the vacuum is supplied via a vacuum tube joined to the suction cup and carried by the slider; and
manually extending and retracting the handgrip to slide the slider along the bendable guide rail to rotate the heart.

\* \* \* \* \*